United States Patent [19]

Mahl et al.

[11] 4,355,021

[45] Oct. 19, 1982

[54] VIRUCIDAL WIPE AND METHOD

[75] Inventors: Mearl C. Mahl, Racine; Elliot C. Dick, Madison; George R. Walter, Jr., Racine, all of Wis.

[73] Assignee: S. C. Johnson & Son, Inc., Racine, Wis.

[21] Appl. No.: 201,960

[22] Filed: Oct. 29, 1980

[51] Int. Cl.³ .................. A61K 9/70; A61F 13/00; A61L 15/03; A61K 33/18
[52] U.S. Cl. .................................. 424/28; 424/150
[58] Field of Search ........................... 424/28, 150

[56] References Cited

U.S. PATENT DOCUMENTS

| | | | |
|---|---|---|---|
| 224,084 | 2/1880 | Gorslene | 424/150 |
| 302,073 | 7/1884 | Wheeler | 424/28 |
| 688,859 | 12/1901 | Just | 424/28 |
| 2,390,391 | 12/1945 | Ritter | 424/28 |
| 2,927,914 | 3/1960 | Hosmer et al. | 424/28 |
| 2,933,431 | 4/1960 | Sperouleas | 424/28 |
| 3,264,188 | 8/1966 | Gresham | 424/28 |
| 3,325,003 | 6/1967 | Bilezerian | 424/28 |
| 3,401,005 | 9/1968 | Katz | 424/28 |
| 4,045,364 | 8/1977 | Richter | 424/150 X |
| 4,207,310 | 6/1980 | Langford | 424/150 |

FOREIGN PATENT DOCUMENTS

| | | | |
|---|---|---|---|
| 588532 | 11/1933 | Fed. Rep. of Germany | 424/28 |
| 2524388 | 1/1976 | Fed. Rep. of Germany | 424/150 |
| 51-101124 | 9/1976 | Japan | 424/150 |
| 76501913 | of 1914 | United Kingdom | 424/28 |
| 382572 | 10/1932 | United Kingdom | 424/28 |
| 399986 | 10/1933 | United Kingdom | 424/28 |

*Primary Examiner*—Shep K. Rose

[57] ABSTRACT

A substantially dry, impregnated wipe having therein iodine and means for retaining the iodine from escape therefrom, the iodine being present in an amount from about 1% to about 15% by weight of the wipe and in an amount sufficient to provide virucidal activity. The iodine is preferably present in an amount of from about 2% to about 5%. A flexible paper substrate is preferred, and the most preferred substrate is facial tissue. The iodine retaining means is preferably a suitable stabilizing surfactant present in an amount sufficient to complex the iodine, but preferably not substantially in excess of an amount sufficient to complex the iodine. A highly preferred stabilizing surfactant is polyoxyethylene (40) sorbitol septaoleate, present in weight ratio to iodine of from about 1:3 to about 2:1, and most preferably about 1:2.

A method of reducing transmission of respiratory viral infections, which includes providing a substantially dry nasal wipe material of the type described and contacting such material with nasal surfaces in the presence of nasal discharge, and, preferably, thereafter wiping to dry hand surfaces with such material.

13 Claims, No Drawings

VIRUCIDAL WIPE AND METHOD

FIELD OF THE INVENTION

This invention is related to the control of viral infections such as respiratory viral infections. In particular, the invention is related to the field of wipes used by persons having viral infections, such as tissues used by persons infected with the common cold.

BACKGROUND OF THE INVENTION

The common cold is a major worldwide health problem. It has been reported that during a recent year common colds occurred in the United States an average of 3.9 times per person and led to an average restriction in activity of 1.2 days per person. The magnitude of the problem is apparent. Losses in productivity, expenditures for so-called "cold remedies" and doctor visits, complications such as sinusitis, and the human misery involved make the common cold a major public health problem.

Little progress has been made toward controlling or curing the common cold. Virtually all new products dealing with the common cold are directed toward relieving the symptoms. And, prevention and/or cure of viral respiratory infections by the usual means—vaccination and chemotherapy—seem out of reach at present.

The large number of respiratory infection virus types make a respiratory infection virus vaccine appear, at present, to be unlikely at best. Rhinoviruses are the principal common cold viruses. There are about 110 different rhinovirus types alone, as well as the influenza and parainfluenza viruses, respiratory syncytial viruses, coronaviruses, and others.

Chemotherapy and chemoprophylaxis do not offer a practical answer either since, at present, there are no practical agents useful against the common cold. Large doses of ascorbic acid, which have been advocated for both prevention and treatment of the common cold, have not been shown effective; the results of controlled experiments have been equivocal at best.

A major obstacle for vaccines or chemical treatments against the common cold is that, unlike many other diseases, both virus acquisition and the disease process occur on the respiratory mucosal surfaces. While this fact may make the common cold difficult to prevent and cure, it has widely been thought that it makes the common cold very easy to transmit and that transmission occurs in many ways. However, in recent years, considerable evidence has been collected showing that respiratory viral infections are much more difficult to spread than was commonly believed.

Various experiments have shown that, generally speaking, only those persons who have relatively severe colds and are shedding rather large amounts of virus seem capable of transmitting their infections to others. Although it is common for physicians and their patients to think of respiratory illnesses as being very contagious, studies have shown that transmission may be surprisingly difficult unless there is considerable intimacy. It was found that inter-family spread was very sporadic, while intra-family dissemination of respiratory viruses was more likely.

Substantial data have shown that infection is likely to occur by contact self-inoculation, that is, the transfer of viruses from a person's virus-contaminated fingers to his own nasal or conjunctival surfaces. This is a process which seems more likely to occur in situations in which there is considerable intimacy or prolonged association. Rhinovirus contamination of hands occurs frequently during rhinovirus colds and it has been shown that rhinoviruses survive well on skin and environmental surfaces. Finger-to-nose and finger-to-eye movements are performed frequently, either consciously or unconsciously, by both adults and children, and these actions are capable of initiating infection if the fingers were previously contaminated.

Transmission is likely to occur, for example, when a parent grossly soils his hands with nasal effluent while wiping the nose of a child and later contaminates his own nasal mucosa or conjunctiva by self-inoculation. Transmission can also occur if an infected family member contaminates his fingers by contact near or insertion into his nares, and then such contamination either directly or indirectly reaches the fingers of a healthy family member who thereafter inserts them into his own nares or with them contacts his conjunctivas.

The developments over the last several years have led to a recognition that the spread of respiratory viral infections may be interruptable more easily than had previously been believed, by eliminating infectious viruses from hands and environmental surfaces to reduce the self-inoculation which otherwise would occur during conscious or unconscious hand movements. It has been noted that infectious viruses could be eliminated from the hands by more frequent hand washing. Frequent hand washing could be specifically promoted for those having colds, particularly after coughing, sneezing, or attending to the profuse nasal discharge that may accompany common colds.

However, avoiding or significantly reducing the conscious or unconscious hand-to-face motions that are so common presents a difficult, if not insurmountable, problem. Even though hand washing might be frequent, the normal hand-to-face movements will continue to cause the frequent transmission of respiratory viral infections through the spread of virus from the infected person and the self-inoculation of the healthy person.

BRIEF SUMMARY OF THE INVENTION

This invention is directed toward reducing the transmission of viral infections, such as respiratory viral infections, and, in particular, achieving such reduction without significantly changing normal behavioral patterns. A substantially dry, flexible, impregnated wipe having virucidal properties against common cold viruses is provided.

The virucidal wipe of this invention is impregnated with iodine and means for retaining the iodine on the wipe. The iodine is present in an amount of about 1.0–15% by weight of the product and in an amount sufficient to provide virucidal activity. The iodine is preferably present in an amount of about 2–5%. A flexible paper substrate, most preferably facial tissue, is used. The iodine is preferably retained within the wipe with a suitable stabilizing surfactant present in an amount sufficient to complex the iodine, but preferably not substantially in excess of an amount sufficient to complex the iodine. The most highly preferred stabilizing surfactant is polyoxyethylene (40) sorbitol septaoleate, present in weight ratio to iodine of about 1:3 to 2:1. The virucidal wipe of this invention retains its virucidal properties over substantial periods of time, in spite of the well-known volatility of iodine. With proper packaging, as described later, the wipe of this invention can retain its virucidal properties during normal storage and shelf life.

The invention further involves a method of reducing the transmission of respiratory viral infections. This unique method involves the steps of providing a substantially dry nasal wipe material of the type described above and contacting such material with nasal surfaces in the presence of nasal discharge. The free iodine encountering live viruses kills the viruses and leaves facial areas near the nares substantially free of live viruses so that subsequent contact by the fingers will not lead to transmission of the disease. Preferred embodiments of this method include the additional step of wiping to dry hand surfaces with such material. This tends to eliminate live viruses which may have reached the user's hands as he captures the nasal secretions.

The effectiveness of the virucidal wipe of this invention and of the method of this invention for reducing the transmission of respiratory viral infections has been tested in clinical tests conducted in Antartica during 1979 and 1980.

OBJECTS OF THE INVENTION

An object of this invention is to provide a dry virucidal wipe for preventing or diminishing virus contamination of human body surfaces.

Another object of this invention is to help reduce the number of occurrences of respiratory viral infections such as the common cold.

Another object of this invention is to provide a nasal tissue which prevents or reduces the transmission of respiratory viral infections without substantially changing behavioral patterns.

Another object of this invention is to provide a nasal tissue which can eliminate or reduce the contamination of the user's face and hands during the capture of nasal secretions.

Another object of this invention is to provide a nasal tissue which prevents the contamination of environmental surfaces by contact with the hands of a person having a respiratory viral infection.

Still another object of this invention is to provide a method for reducing the transmission of respiratory viral infections which does not require substantial changes in the behavior of infected persons.

Another object of this invention is to provide a dry nasal tissue having a virucidal effect when used in the manner in which nasal tissues of the prior art are normally used.

Another object of this invention is to provide a dry virucidal nasal wipe which maintains its virucidal capability over substantial periods of time.

These and other objects of the invention will be apparent from the foregoing portions and the following detailed specification.

DETAILED DESCRIPTION OF PREFERRED EMBODIMENTS

The substrate material used in the virucidal wipe of this invention is a flexible absorbent material of a type suitable for wiping the face and hands. Paper is a preferred substrate material and the most preferred substrate material is facial tissue, which is normally a single- or multiple-ply light basis weight soft creped wadding or air-formed material. Other acceptable materials include spun-bonded and melt-blown nonwovens made from thermoplastic fibers such as polyolefins.

A multiple-ply creped wadding facial tissue is especially preferred because of its strength. An example of a particularly satisfactory material is the three-ply creped wadding used by Kimberly-Clark Corporation, of Neenah, Wisconsin, for its Man-Sized KLEENEX tissues.

The virucidal activity of the virucidal wipes of this invention is provided by iodine. The iodine used in making the virucidal wipes may be obtained in its crystalline form, and is available from a number of sources. The substrate may be impregnated with iodine using a method which will be described hereinafter.

Iodine is present in the wipes of this invention in an amount of from about 1.0% to about 15% by weight of the impregnated wipe. The iodine is most preferably present in an amount of from about 2% to about 5% by weight of the impregnated wipe. If the iodine level is below about 1% by weight of the impregnated wipe, the virucidal capabilities of the wipe may be insufficient. Iodine levels in excess of about 15% could tend to stain the skin, cause an irritating pungent odor, or weaken the paper substrate. When iodine is present in an amount within the preferred range of 2–5%, the most effective balance of efficacy, stability, cosmetic concerns, and sensory concerns is achieved.

An important constituent of the virucidal wipe of this invention is another part of the impregnant—a means for retaining the iodine from escape from the wipe by volatilization. This is of particular importance because of the well-known highly volatile nature of iodine. The retaining means is preferably a stabilizing surfactant, which serves to complex the iodine and thus hold it in the dry virucidal wipe during storage and prior to use.

Several surfactants have been found to perform satisfactorily as the stabilizing surfactant in this invention. These include: linoleic diethanolamide, a nonionic surfactant available from Mona Industries, Inc., Patterson, N.J., under the trademark MONAMID 15-70W; the sodium salt of undecylenic acid monoethanolamide sulfosuccinate, a nonionic surfactant available from Rewo Chemical, Inc., Mauldin, S.C., under the trademark REWOCID DU-185; an ethoxylated polymethylsiloxane having nonionic surfactant qualities available from Union Carbide Corporation, New York, N.Y., under the trademark L-77 Silicone; and ditallow (diethylenetriamine) ethyleneoxide dimethyl sulfate quaternary, a cationic surfactant available from Sherex Chemical Company, of Dublin, Ohio, under the trademark VARISOFT 222. A highly preferred stabilizing surfactant is polyoxyethylene (40) sorbitol septaoleate, a nonionic surfactant available from ICI Americas, Inc., Wilmington, Del., under the trademark ARLATONE T.

Any surfactant which is acceptable for use on human skin, which serves to complex the iodine but to allow its subsequent release from the complex, and which would not impart undesirable attributes (e.g., stickiness, hardness, or odor) to the substrate would be satisfactory for use in this invention. A suitable stabilizing surfactant is used in an amount sufficient to complex the iodine and preferably not substantially in excess of an amount sufficient to complex the iodine.

The stabilizing surfactant should be chosen and used in an amount such that when the dry wipe is wetted by nasal secretions or otherwise, the wetness releases iodine from the complex thus making it available to kill rhinoviruses or other infectious viruses in contact therewith. The stabilizing surfactant would be used to excess if insufficient amounts of iodine are made available upon wetting to provide the desired virucidal activity or if the virucidal wipe became too slippery in character such that it feels substantially different than a nasal tissue of the prior art.

An excessive amount of surfactant will also tend to make the dry wipe boardy, that is, relatively hard and inflexible. Appropriate amounts of stabilizing surfactant or other stabilizing means will depend upon the surfactant or other means used. The most highly preferred stabilizing surfactant, polyoxyethylene (40) sorbitol septaoleate (ARLATONE T) may be used in a weight ratio to iodine of from about 1:3 to about 2:1. Lesser amounts would be insufficient to adequately complex the iodine and to preserve it for later virucidal activity. Greater amounts would tend to capture the iodine too much, thus inhibiting its later virucidal activity, and/or produce unsatisfactory surface characteristics, particularly when the wipe is wet.

Other constituents may be included within the impregnant of the virucidal wipe of this invention. For example, small amounts of perfume are preferably included in the impregnant to improve the sensory qualities of the virucidal wipe. A wide variety of commercially available perfumes would be acceptable, and these would be apparent to those skilled in the art and familiar with this invention.

The virucidal wipe of this invention may be made without any heat processing or unusual processing steps. A preferred method of producing the wipe involves preparing an iodine intermediate solution using a fugitive solvent, impregnating a paper or other substrate with such intermediate, and then drying the impregnated substrate to remove the fugitive solvent.

The iodine intermediate used in making a preferred embodiment of this invention is prepared by adding resublimed iodine crystals, an acceptable stabilizing surfactant, and a perfume to a fugitive solvent. This mixture is thoroughly stirred, preferably for about 30 minutes, but at least until it is in solution. The substrate material which has been selected for use is then impregnated with this iodine intermediate solution using any of a variety of impregnating methods.

Acceptable impregnating methods include printing, dipping, and spraying. Such operations are preferably carried out on a web of substrate material as it extends over processing equipment between a supply roll and a take-up roll. The impregnated web passes an application point where it is printed, dipped or sprayed with the iodine intermediate solution. If a dipping process is used, the web may thereafter be squeezed to control the amount of impregnant. The amount of impregnant applied using a printing or spraying step can be controlled directly at the application point.

After application of the iodine intermediate, the web is dried. Drying is preferably carried out by allowing the impregnated web to remain for a period of time in a ventilated area before it is wound onto a take-up roll. Good ventilation in the drying area facilitates the removal of fugitive solvent vapors. The dried web of virucidal wipe material is then wound onto a roll and may thereafter be converted to individual wipes or wipe material webs of various sizes and shapes.

Ethyl alcohol is a preferred fugitive solvent for use in the production of the virucidal wipe of this invention. Ethyl alcohol dissolves the iodine crystals and stabilizing surfactant easily and vaporizes quickly during the drying step. Other fugitive solvents could be used, including alcohols other than ethanol, diethyl ether, water, glycerol, and mixtures of alcohol and water. Acceptable fugitive solvents must adequately dissolve the iodine crystals and other constituents of the iodine intermediate, must be capable of drying in a reasonable period of time, and must be toxicologically acceptable.

The drying step may not remove all moisture from the virucidal wipe material. However, the virucidal wipe of this invention should be substantially free of moisture, that is, feel substantially dry (no more than a slight feel of moistness) rather than wet to the user. For example, a virucidal wipe having a water content of about 6% by weight of the wipe, or even more, would feel relatively dry to the touch. The wipe should be perceived by the user to be not substantially different than facial tissues. The amount of moisture which can be in the wipe of this invention is dependent upon the substrate which is used.

The virucidal wipe material can be made using other methods, and such would be apparent to those skilled in the art who are familiar with this invention. Appropriate methods will be dictated to some extent by the means used to retain the iodine from escaping from the wipe.

The virucidal wipe(s) of this invention should be packaged in a container which is substantially impervious to iodine vapors. Acceptable materials for such packaging include: polyethylene terephthalate polymers, such as those available under the trademark MYLAR (100M30 and 75M30) from E. I. DuPont de Nemours and Company, Wilmington, Del.; various copolymers of vinylidene chloride and vinyl chloride, such as those available under the trademark SARAN from Dow Chemical Company, Midland, Mich.; and a copolymer of acrylonitrile with methylacrylate, such as that available under the trademark BAREX 210 from Vistron Corporation, Cleveland, Ohio. Other acceptable iodine impervious materials include metal foils, although with certain foils coating would be required to avoid corrosion.

As noted above, the virucidal wipes of this invention may be in various sizes and shapes. And, the packaging for the virucidal wipes of this invention can be in many forms, including flexible film pocket packs, pop-up containers of the type having a slit orifice which seals on itself, coated foil pouches, and any of a variety of covered containers. Regardless of the packaging form, the use of an iodine-impervious material will serve to maintain the virucidal activity of the wipes for extended periods of time.

An important aspect of this invention is the establishment of a method for interrupting the normal transmission of respiratory viral infections without significantly modifying the behavioral patterns of infected persons. By using the virucidal wipes of this invention instead of regular facial tissues or handkerchiefs, substantial reductions is the number of new respiratory viral infections have been achieved in a controlled population. Infected persons simply use the virucidal wipe of this invention to wipe their noses and to otherwise capture the limited or profuse nasal secretions which occur during the common cold. If the user's hands become wet with such nasal secretions, the virucidal wipe materials of this invention can be used to remove such wetness.

The virucidal wipe of this invention kills live viruses within the contacted areas of the nares, on the areas around the nose, and on the hands, and thus breaks what is now believed to be a primary chain of transmission of respiratory viral infections. A high percentage of nasal discharge is water; such water releases iodine in the virucidal wipe making it available to kill viruses in such discharge and on contacted areas. In the preferred embodiments which use a stabilizing surfactant, the iodine is free from its complex to perform its virucidal function. Once the virucidal wipe is discarded, such as into a wastebasket, it will continue to kill live viruses captured by the wipe, thus reducing a reservoir of infectious particles and lowering the possibility of transmission by later contact.

The following are examples of specific virucidal wipes in accordance with this invention:

EXAMPLE I

An iodine intermediate is made using the procedures outlined above to solubilize the following:

| | |
|---|---|
| Resublimed iodine crystals | 727.2 g |
| ARLATONE T (polyoxyethylene (40) sorbitol septaoleate) | 363.6 g |
| Perfume | 72.7 g |
| Ethyl alcohol (absolute) | 17.0 kg. |

About 90% of this solution is used to impregnate 5500 feet of a three-ply creped wadding facial tissue of 12-inch width, using a printing process. This web is thereafter air-dried and converted into acceptable lengths to provide virucidal wipes. The resulting wipe has an iodine content of about 3% by weight and a stabilizing surfactant content of about 1.5%. The dry wipe has aproximately the same softness and surface characteristics as a facial tissue of the prior art, and exhibits good virucidal activity to interrupt the spread of respiratory viral infections.

EXAMPLE II

An iodine intermediate is made by stirring the following to solution:

| | |
|---|---|
| Resublimed iodine crystals | 0.2 g |
| ARLATONE T | 0.1 g |
| Perfume | 0.01 g |
| Diethyl Ether | 99.69 g. |

Five individual 11×12 inch three-ply creped wadding facial tissues are dipped into and absorb essentially all of this intermediate and are thereafter air-dried. The resulting wipes have about 1% iodine and about 0.5% stabilizing surfactant. These wipes exhibit some virucidal activity, but are less effective than the wipes of Example I.

EXAMPLE III

An iodine intermediate is made using the mixing procedures of Example II and the following constituents:

| | |
|---|---|
| Resublimed iodine crystals | 0.4 g |
| ARLATONE T | 1.2 g |
| Perfume | 0.02 g |
| Ethyl alcohol | 98.38 g. |

This intermediate is impregnated into the substrate material of Example I to the extent which after drying yields wipes having an iodine content of about 2% and stabilizing surfactant content of about 6%. These wipes exhibit virucidal characteristics, but their surface characteristics are somewhat marginal.

EXAMPLE IV

An iodine intermediate is made using the mixing procedures of Example II and the following constituents:

| | |
|---|---|
| Resublimed iodine crystals | 4.0 g |
| ARLATONE T | 2.0 g |
| Perfume | 0.4 g |
| Ethyl alcohol | 93.6 g. |

This intermediate is impregnated into the substrate material of Example I to the extent which after drying yields wipes having an iodine content of about 15% and a stabilizing surfactant content of about 7.5%. The wipes exhibit excellent virucidal qualities, but staining of the skin is possible and there is a pungent odor which some might consider unacceptable.

EXAMPLE V

An iodine intermediate is made using the mixing procedures of Example II and the following constituents:

| | |
|---|---|
| Resublimed iodine crystals | 0.4 g |
| MONAMID 15-70W (linoleic diethanolamide) | 0.4 g |
| Perfume | 0.04 g |
| Water | 99.16 g. |

This intermediate is impregnated into a heavy, single-ply creped wadding facial tissue substrate to the extent which after drying yields wipes having about 2% iodine and about 2% stabilizing surfactant. Drying takes a longer period since the fugitive solvent is water. The wipes exhibit good virucidal and surface qualities.

EXAMPLE VI

An iodine intermediate is made using the mixing procedures of Example II and the following constituents:

| | |
|---|---|
| Resublimed iodine crystals | 0.6 g |
| REWOCID DU-185 (the sodium salt of undecylenic acid monoethanolamide) | 0.6 g |
| Perfume | 0.06 g |
| Ethyl alcohol | 98.74 g. |

This intermediate is impregnated into a two-ply air-formed facial tissue substrate to the extent which after drying yields wipes having about 3% iodine and about 3% stabilizing surfactant. They have good virucidal and surface qualities.

EXAMPLE VII

An iodine intermediate is made using the mixing procedures of Example II and the following constituents:

| | |
|---|---|
| Resublimed iodine crystals | 0.8 g |
| L-77 Silicone (an ethoxylated polymethylsiloxane from Union Carbide Corporation) | 0.8 g |
| Perfume | 0.08 g |
| Ethyl alcohol | 98.32 g. |

This intermediate is impregnated into the substrate material of Example I to the extent which after drying yields wipes having about 4% iodine and about 4% stabilizing surfactant. These wipes have good virucidal and surface qualities.

EXAMPLE VIII

An iodine intermediate is made using the mixing procedures of Example II and the following constituents:

| | |
|---|---|
| Resublimed iodine crystals | 0.6 g |
| VARISOFT 222 (ditallow (diethylene-triamine) ethoxyleneoxide dimethyl sulfate quaternary) | 0.6 g |
| Perfume | 0.06 g |
| Ethyl alcohol | 98.74 g. |

This intermediate is impregnated into soft woven cotton cloth material to the extent which after drying yields wipes having about 3% iodine and about 3% stabilizing surfactant. The wipes have good virucidal qualities.

EXAMPLE IX

An iodine intermediate is made using the mixing procedures of Example II and the following constituents:

| | |
|---|---|
| Resublimed iodine crystals | 1.1 g |
| ARLATONE T | 0.55 g |
| Perfume | 0.1 g |
| Ethyl alcohol | 98.25 g. |

This intermediate is impregnated into the substrate material of Example I to the extent which after drying yields wipes having about 5% iodine and about 2.5% stabilizing surfactant. These wipes exhibit excellent virucidal and surface characteristics.

While in the foregoing specification this invention has been described in relation to certain preferred embodiments and many details have been set forth for purpose of illustration, it will be apparent to those skilled in the art that the invention is susceptible to additional embodiments and that certain of the details described herein can be varied considerably without departing from the basic principles of the invention.

We claim:

1. In a method for removal of respiratory viral infection-related nasal secretions of the type including the step of wiping nasal surfaces with a dry, flexible, absorbent wipe material, the improvement comprising:
   providing such wipe material having substrate means with impregnant therein which in contact with moisture will release iodine on said substrate means in an amount sufficient to provide virucidal activity, said wipe material being substantially free of moisture before use and said impregnant retaining the iodine from escape from said wipe material before use;
   contacting said wipe material with nasal surfaces to remove nasal discharge therefrom, thereby moistening said wipe material to release on said wipe material a virucidally sufficient amount of iodine; and
   thereby killing with said iodine viruses on the contacted surfaces,
   whereby transmission of respiratory viral infection is interrupted without significantly modifying behavioral patterns of infected persons.

2. The method of claim 1 wherein said iodine on said dry wipe material is present in an amount of from about 1.0 to about 15% by weight of said dry wipe material.

3. The method of claim 2 wherein said iodine is present in an amount of from about 2% to about 5%.

4. The method of claim 1 including the subsequent step of wiping to dry hand surfaces with said wipe material.

5. The method of claim 2 wherein the flexible substrate is facial tissue.

6. The method of claim 1 wherein said impregnant includes iodine in an amount of from about 1.0 to about 15% by weight of said dry wipe and a suitable stabilizing surfactant in an amount sufficient to complex said iodine.

7. The method of claim 6 wherein the surfactant is not substantially in excess of an amount sufficient to complex the iodine.

8. The method of claim 7 wherein the iodine is present in an amount of from about 2% to about 5%.

9. The method of claim 7 wherein the surfactant is polyoxyethylene (40) sorbitol septaoleate and is present in a weight ratio to iodine of from about 1:3 to about 2:1.

10. The method of claim 9 wherein the iodine is present in an amount of from about 2% to about 5%.

11. The method of claim 10 wherein the flexible substrate is facial tissue.

12. The method of claim 11 including the subsequent step of wiping to dry hand surfaces with said wipe material.

13. The method of claim 12 wherein the ratio of the surfactant to the iodine is about 1:2.

* * * * *